United States Patent
Guo

(10) Patent No.: US 11,879,615 B1
(45) Date of Patent: Jan. 23, 2024

(54) TOUCHABLE SWITCH ELECTRONIC CANDLE WITH FRAGRANCE DISPERSING FUNCTION

(71) Applicant: Chang Zhou Man Mei Industrial Co., Ltd., Changzhou (CN)

(72) Inventor: Lei Guo, Changzhou (CN)

(73) Assignee: CHANG ZHOU MAN MEI INDUSTRIAL CO., LTD., Changzhou (CN)

( * ) Notice: Subject to any disclaimer, the term of this patent is extended or adjusted under 35 U.S.C. 154(b) by 0 days.

(21) Appl. No.: 17/954,368

(22) Filed: Sep. 28, 2022

(30) Foreign Application Priority Data

Aug. 17, 2022 (CN) .......................... 202222165209.6

(51) Int. Cl.
*F21V 23/04* (2006.01)
*F21S 6/00* (2006.01)
*F21V 23/00* (2015.01)
*H03K 17/96* (2006.01)

(52) U.S. Cl.
CPC .......... *F21V 23/0485* (2013.01); *F21S 6/001* (2013.01); *F21V 23/003* (2013.01); *F21V 23/007* (2013.01); *F21V 23/045* (2013.01); *H03K 17/962* (2013.01)

(58) Field of Classification Search
CPC .. F21V 23/0485; F21V 23/003; F21V 23/007; F21V 23/045; F21S 6/001; H03K 17/962
See application file for complete search history.

(56) References Cited

FOREIGN PATENT DOCUMENTS

| CN | 205245075 U | * | 5/2016 | |
|---|---|---|---|---|
| CN | 207162403 U | * | 3/2018 | |
| DE | 102016008825 A1 | * | 12/2017 | ............... A61L 2/00 |

* cited by examiner

*Primary Examiner* — Abdullah A Riyami
*Assistant Examiner* — Syed M Kaiser
(74) *Attorney, Agent, or Firm* — Bayramoglu Law Offices LLC

(57) ABSTRACT

A touchable switch electronic candle with fragrance dispersing function includes a master control circuit and a touch switch circuit. The touch switch circuit is used to detect a touch signal and generate a new instantaneous voltage difference, and a touch switch chip captures the voltage difference to generate a signal. The master control circuit is used to receive the signal generated by the touch switch circuit and change the light emission status of candle lamp beads. In the touch switch circuit, the human body touches or approaches a touch end, then the capacitance fluctuation occurs, thereby generating a new instantaneous voltage difference, and the touch switch chip captures this voltage difference, then generates a signal, and sends the signal to the master control circuit; and the master control circuit is responsible for receiving the signal sent by the touch switch circuit and controlling the light on.

14 Claims, 5 Drawing Sheets

TOUCHABLE SWITCH ELECTRONIC CANDLE WITH FRAGRANCE DISPERSING FUNCTION

CROSS REFERENCE TO THE RELATED APPLICATIONS

This application is based upon and claims priority to Chinese Patent Application No. 202222165209.6, filed on Aug. 17, 2022, the entire contents of which are incorporated herein by reference.

TECHNICAL FIELD

The present disclosure relates to the technical field of electronic candle, in particular to a touchable switch electronic candle with fragrance dispersing function.

BACKGROUND

Existing candles are made from paraffin wax, which produces volatile gas when burned, thereby polluting the air. Moreover, under the current advocacy of environmental protection, resource conservation or rational use of resources, electronic candles have emerged as the times require.

The manner of switching the existing electronic candle is relatively traditional, it is generally controlled by a press-type or push-type switch, the operation process lacks interest, and the existing electronic candle generally does not have fragrance dispersing function. Therefore, provided is a touchable switch electronic candle with fragrance dispersing function.

SUMMARY

The purpose of the present disclosure is to solve the shortcomings of the prior art, and provided is a touchable switch electronic candle with fragrance dispersing function.

In order to achieve the above purpose, the present disclosure adopts the following technical solutions:

a touchable switch electronic candle with fragrance dispersing function, including a master control circuit and a touch switch circuit, the touch switch circuit is used to detect a touch signal and generate a new instantaneous voltage difference, and a touch switch chip captures the voltage difference to generate a signal; the master control circuit is used to receive the signal generated by the touch switch circuit and change the light emission status of candle lamp beads;

the touch switch circuit includes a touch switch chip U2, a resistor R1, a touch end TOUCH, a first capacitor C1, a second capacitor C2, a supply voltage VDD and a grounding end, the supply voltage VDD is connected to a pin 1 of the touch switch chip U2, a pin 5 of the touch switch chip U2 is connected to the grounding end, the second capacitor C2 is connected between the pin 1 and pin 5 of the touch switch chip U2, the first capacitor C1 is connected between the pin 5 of the touch switch chip U2 and a pin 7 thereof, and the touch end TOUCH is connected in series with the resistor R1 and then connected to a pin 8 of the touch switch chip U2; and the master control circuit includes a master control chip U1, a light emitting diode D1, a crystal oscillator Y1, the supply voltage VDD and the grounding end, the supply voltage VDD is connected to a pin 1 of the master control chip U1, a pin 5 and a pin 6 of the master control chip U1 are connected to the light emitting diode D1, the light emitting diode D1 is connected to the grounding end, the crystal oscillator Y1 is connected between a pin 2 and a pin 3 of the master control chip U1, and a pin 8 of the master control chip U1 is connected to the pin 3 of the touch switch chip U2.

Preferably, the master control circuit further includes an infrared receiver IR, and the infrared receiver IR is connected to a pin 4 of the master control chip U1.

Preferably, further included is a fragrance dispersing block, and the inside of the fragrance dispersing block is filled with essence.

Preferably, further included is a shell body, the outer side of the shell body is provided with a wax layer, and the top end of the wax layer is provided with a groove for accommodating the fragrance dispersing block.

Preferably, the surface of the fragrance dispersing block is a smooth mirror surface, and fragrance and filler constituting fragrance dispersing block are integrally formed.

Preferably, the fragrance dispersing block is porous, and the fragrance is filled in pores of the filler constituting the fragrance dispersing block; and further included is an essence urging mechanism, and the essence urging mechanism facilitates the volatilization of the essence in the fragrance dispersing block.

Preferably, the upper end of the fragrance dispersing block is covered with a decorative layer with micro-pores, and the surface of the decorative layer is a smooth mirror surface.

Preferably, the essence urging mechanism is a micro-fan, the micro-fan is provided in the inside of the shell body, and the outlet end of the micro-fan is connected to the fragrance dispersing block through an air outlet pipe.

Preferably, the essence urging mechanism is an electric heating wire, the top end of the shell body is provided with a heat insulation block, the electric heating wire is arranged on the top end of the heat insulation block, and the electric heating wire is in contact with the fragrance dispersing block.

Preferably, the inside of the shell body is provided with a battery bin, the master control circuit is located inside the shell body, the touch switch circuit is located outside the shell body, the top end of the shell body is provided with a candle head, and the light emitting diode D1 is located inside the candle head.

The beneficial effects of the present disclosure are as follows:

1. The electronic candle is provided with a master control circuit and a touch switch circuit, in the touch switch circuit, the human body touches or approaches a touch end, then the capacitance fluctuation occurs, thereby generating a new instantaneous voltage difference, and a touch switch chip captures this voltage difference, then generates a signal, and sends the signal to the master control circuit; and the master control circuit is responsible for receiving the signal sent by the touch switch circuit and controlling the light on, and through the mutual cooperation of these two circuits, the use of the electronic candle is convenient and makes the electronic candle have a certain interest.

2. The electronic candle is also provided with a fragrance dispersing block, the fragrance dispersing block (decorative layer) can simulate the visual effect of melting wax water, thereby improving the realism of the electronic candle, and the fragrant block adopts natural volatilization or artificial triggering to emit fragrance, further improving the interest of candles when used.

In the figures: 1. shell body, 11. wax layer, 2. battery bin, 3. master control circuit, 4. touch switch circuit, 5. candle head, 6. fragrance dispersing block, 7. micro-fan, 71. air outlet pipe, 8. decorative layer, 9. heat insulation block, and 10. electric heating wire.

DETAILED DESCRIPTION OF THE EMBODIMENTS

The technical solutions in the examples of the present disclosure will be clearly and completely described below in conjunction with the accompanying drawings in the examples of the present disclosure. Obviously, the described examples are only a part of the examples of the present disclosure, but not all of the examples.

Figure 1:
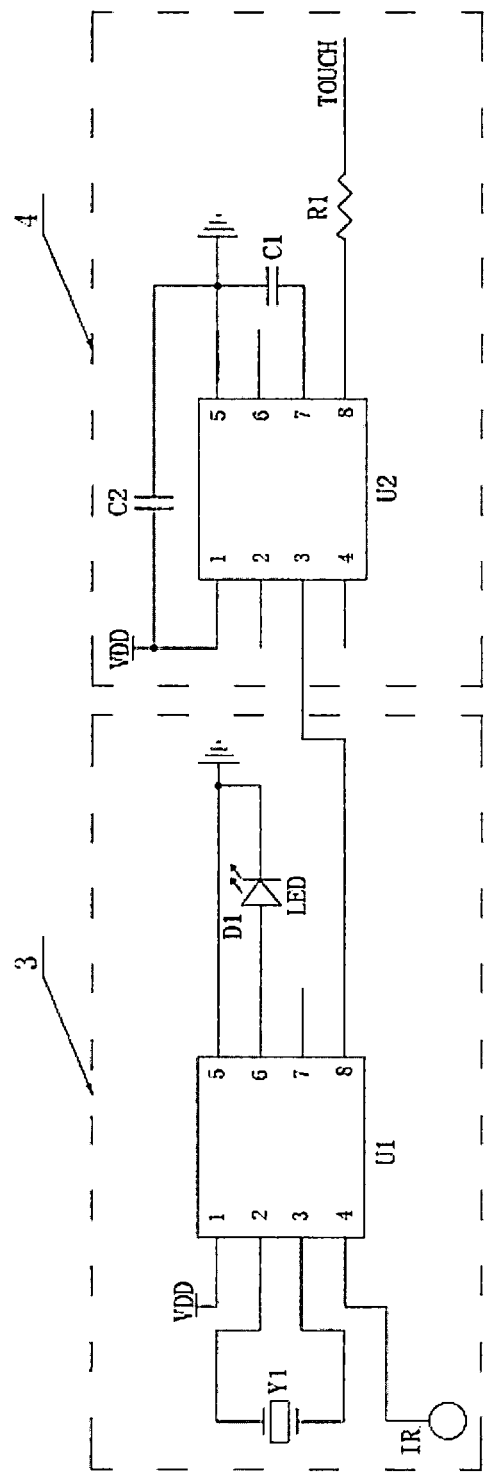
FIG. 1 is a schematic diagram of the circuit connection of a touchable switch electronic candle with fragrant dispersing function provided by the present disclosure.
Figure 2:
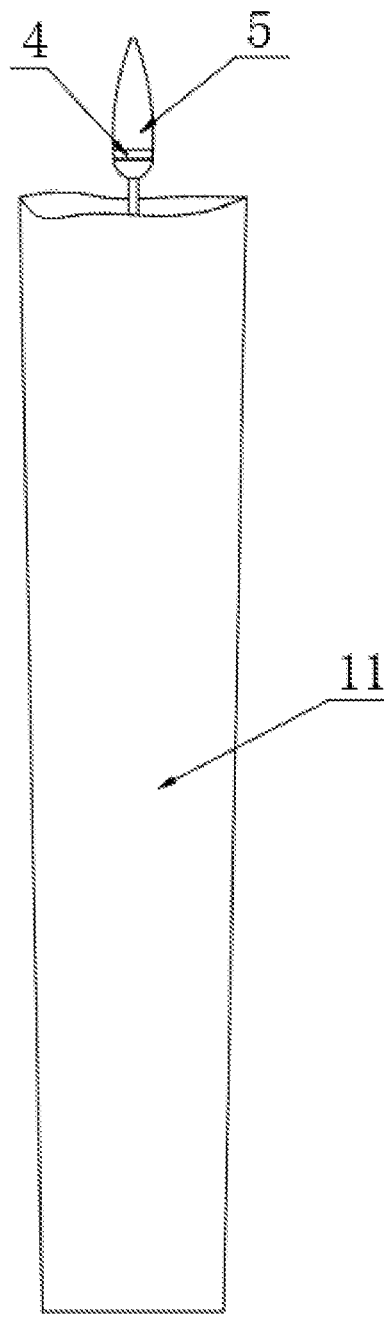
FIG. 2 is a schematic diagram of the front view structure of the touchable switch electronic candle with fragrance dispersing function provided by the present disclosure.
Figure 3:
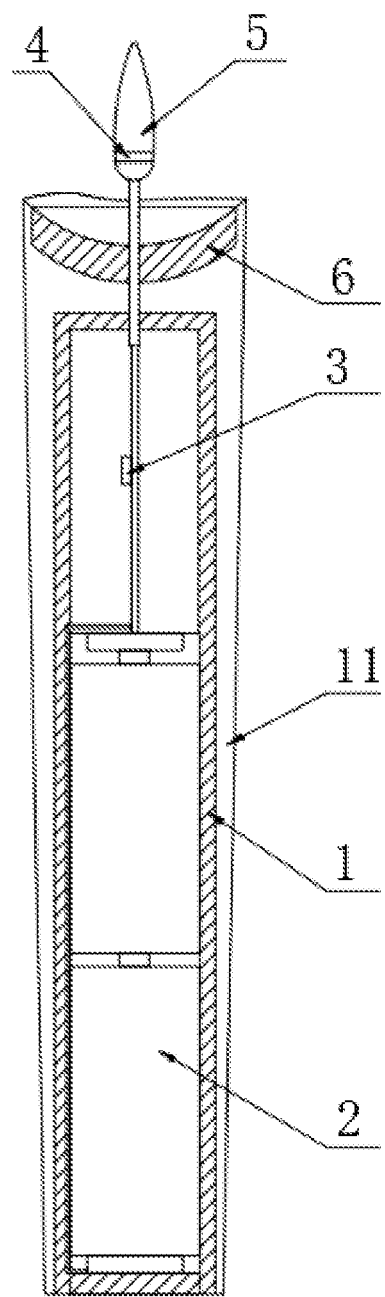
FIG. 3 is a schematic diagram I of the front section structure of the touchable switch electronic candle with fragrance dispersing function provided by the present disclosure.

In example 1, referring to FIGS. 1-3, a touchable switch electronic candle with fragrance dispersing function includes a master control circuit 3 and a touch switch circuit 4, and the touch switch circuit 4 is used to detect a touch signal and generate a new instantaneous voltage difference. A touch switch chip U2 captures the voltage difference and generates a signal. The master control circuit 3 is used to receive the signal generated by the touch switch U2 circuit and change the light emission status of candle lamp beads, and the candle lamp beads generally use LED lamp beads.

The touch switch circuit 3 includes a touch switch chip U2, a resistor R1, a touch end TOUCH, a first capacitor C1, a second capacitor C2, a supply voltage VDD and a grounding end. The supply voltage VDD is connected to a pin 1 of the touch switch chip U2, a pin 5 of the touch switch chip U2 is connected to the grounding end, the second capacitor C2 is connected between the pin 1 and pin 5 of the touch switch chip U2, the first capacitor C1 is connected between the pin 5 of the touch switch chip U2 and a pin 7 thereof, and the touch end TOUCH is connected in series with the resistor R1 and then connected to the pin 8 of the touch switch chip U2. The touch end TOUCH can be arranged on the candle head 5 or on the surface of the candle, which is both decorative and practical.

The master control circuit 3 includes a master control chip U1, a light emitting diode D1, a crystal oscillator Y1, the supply voltage VDD and the grounding end. The supply voltage VDD is connected to a pin 1 of the master control chip U1. A pin 5 and a pin 6 of the master control chip U1 are connected to the light emitting diode D1. The light emitting diode D1 is connected to the grounding end. The crystal oscillator Y1 is connected between a pin 2 and a pin 3 of the master control chip U1. A pin 8 of the master control chip U1 is connected to the pin 3 of the touch switch chip U2.

The master control circuit 3 also includes an infrared receiver IR. The infrared receiver IR is connected to the pin 4 of the master control chip U1. Through the infrared receiver IR, the signal of the infrared remote control can be received to achieve the function of the product being remotely controlled.

Further included is a shell body 1. The outer side of the shell body 1 is provided with a wax layer 11. The top end of the wax layer 11 is provided with a groove for accommodating the fragrance dispersing block 6. The inside of the fragrance dispersing block 6 is filled with essence.

The surface of the fragrance dispersing block 6 is a smooth mirror surface, and fragrance and filler constituting fragrance dispersing block 6 are integrally formed.

The specific method for preparing the fragrance dispersing block 6 is as follows: epoxy resin, or gypsum, or paraffin, or transparent colloid are poured in the groove. Essence is added during the pouring process, solidified in the groove, and combined with the wax body. Through the natural volatilization of the essence (essential oil), the electronic candle in the case of emitting a charming fragrance without being lit, and in the process of use, according to personal needs, the essence can be added at any time.

When pouring, the proportion of the essence is paid attention, which is generally controlled within 1%40% to prevent the essence from overflowing or the fragrance being too strong.

When pouring, first the filler and essence are mixed according to the proportion of 1%-10%, and then the peristaltic canning equipment or manually hold container are used for canning. The canning should not exceed the outside of the groove, and the surface and the wax surface are kept in a plane, which is similar to the visual effect of melting the wax water after burning a real candle.

The inside of the shell body 1 is provided with a battery bin 2. The battery bin 2 generally houses two 1.5 V batteries. The master control circuit 3 is located inside the shell body 1. The touch switch 4 circuit is located outside the shell body 1. The top end of the shell body 1 is provided with a candle head 5. The light emitting diode D1 is located inside the candle head 5.

Figure 4:
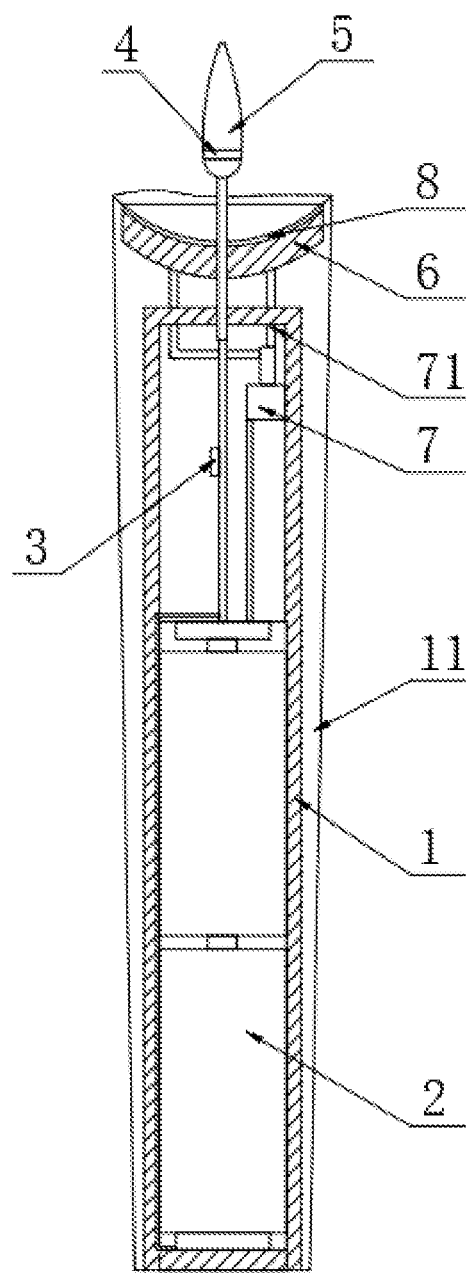
FIG. 4 is a schematic diagram II of the front section structure of the touchable switch electronic candle with fragrance dispersing function provided by the present disclosure.

In example 2, referring to FIG. 4, different from the example 1, the fragrance dispersing block 6 is porous, and the fragrance is filled in pores of the filler constituting the fragrance dispersing block.

Further included is an essence urging mechanism, the essence urging mechanism facilitates the volatilization of the essence in the fragrance dispersing block.

The essence urging mechanism is a micro-fan 7. The micro-fan 7 is arranged in the inside of the shell body 1, and the outlet end of the micro-fan 7 is connected to the fragrance dispersing block 6 through an air outlet pipe 71, that is, a weak airflow is provided to the fragrant dispersing block 6 through the micro-fan 7, so that the essence in the fragrance dispersing block 6 is volatilized.

Figure 5:
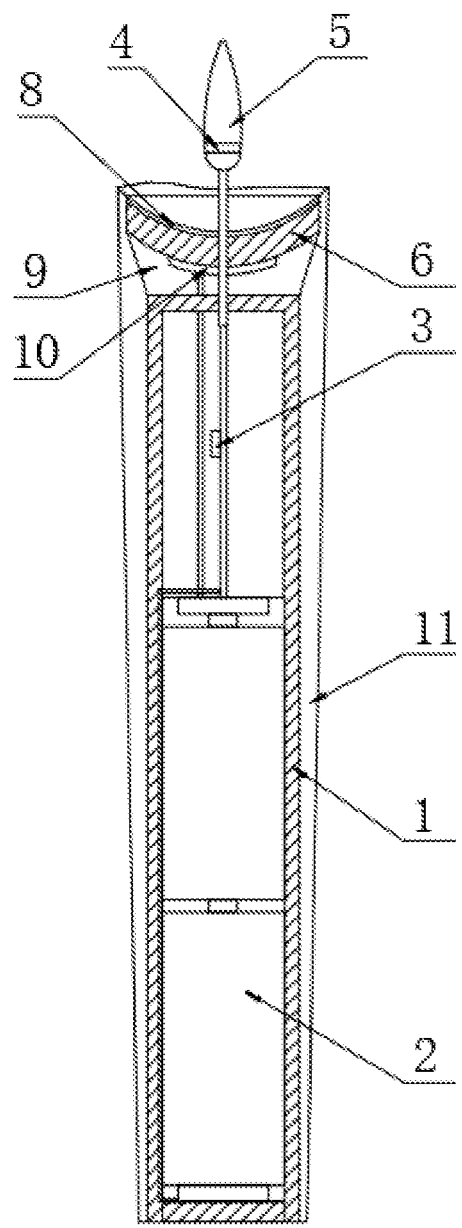
FIG. 5 is a schematic diagram III of the front section structure of the touchable switch electronic candle with fragrance dispersing function provided by the present disclosure.

In example 3, referring to FIG. 5, different from the example 2, the essence urging mechanism is an electric heating wire 10. A heat insulation block 9 is provided at the top end of the shell body 1. The electric heating wire 11 is arranged on the top end of the heat insulation block 9. The electric heating wire 11 is in contact with the fragrance dispersing block 6. The wax layer 11 can be prevented from being melted by the heat insulating block 9 when the heating wire 11 is working, and after the electric heating wire 11 works, the temperature of the fragrance dispersing block 6 can be increased, so that the essence in the fragrance dispersing block 6 is volatilized.

Further, in the examples 2-3, the upper end of the fragrance dispersing block 6 is covered with a decorative layer 8 with micro-pores. The decorative layer 8 can be made from epoxy resin. The visual effect of wax water melting is formed through the decorative layer 8. The surface of the decorative layer is a smooth mirror surface.

In the examples 1-3, the electronic candle is provided with a master control circuit 3 and a touch switch circuit 4. In the touch switch circuit 4, the human body touches or approaches a touch end (distance less than 1 mm), and then the capacitance fluctuation occurs, thereby generating a new instantaneous voltage difference. A touch switch chip captures this voltage difference, then generates a signal, and sends the signal to the master control circuit 3. The master control circuit 3 is responsible for receiving the signal sent by the touch switch circuit 4 and controlling the light on. Through the mutual cooperation of these two circuits, the use of the electronic candle is convenient and makes the electronic candle have a certain interest.

The above description is only a preferred embodiment of the present disclosure, but the protection scope of the present disclosure is not limited to this, and equivalent substitution or changes made by those skilled in the art in accordance with the technical solution and the concept of the present disclosure should be covered within the protection scope of the present disclosure.

What is claimed is:

1. A touchable switch electronic candle with fragrance dispersing function, comprising a master control circuit and a touch switch circuit, wherein the touch switch circuit is used to detect a touch signal and generate a new instantaneous voltage difference, and a touch switch chip captures the new instantaneous voltage difference to generate a signal; the master control circuit is used to receive the signal generated by the touch switch circuit and change a light emission status of candle lamp beads; the touch switch circuit comprises the touch switch chip (U2), a resistor (R1), a touch end (TOUCH), a first capacitor (C1), a second capacitor (C2), a supply voltage (VDD) and a grounding end, wherein the supply voltage (VDD) is connected to first pin (1) of the touch switch chip (U2), fifth pin (5) of the touch switch chip (U2) is connected to the grounding end, the second capacitor (C2) is connected between the first pin (1) and the fifth pin (5) of the touch switch chip (U2), the first capacitor (C1) is connected between the fifth pin (5) of the touch switch chip (U2) and seventh pin (7) of the touch switch chip (U2), and the touch end (TOUCH) is connected in series with the resistor (R1) and then connected to a eighth pin (8) of the touch switch chip (U2); and the master control circuit comprises a master control chip (U1), a light emitting diode (D1), a crystal oscillator (Y1), the supply voltage (VDD) and the grounding end, wherein the supply voltage (VDD) is connected to pin 1 the first pin (1) of the master control chip (U1), fifth pin (5) and pin 6 sixth pin (6) of the master control chip (U1) are connected to the light emitting diode (D1), the light emitting diode (D1) is connected to the grounding end, the crystal oscillator (Y1) is connected between second pin (2) and third pin (3) of the master control chip (U1), and eight pin (8) of the master control chip (U1) is connected to third pin (3) of the touch switch chip (U2).

2. The touchable switch electronic candle with fragrance dispersing function according to claim 1, wherein the master control circuit further comprises an infrared receiver (IR), wherein the infrared receiver IR is connected to fourth pin (4) of the master control chip (U1).

3. The touchable switch electronic candle with fragrance dispersing function according to claim 1, further comprising a fragrance dispersing block, wherein an inside of the fragrance dispersing block is filled with essence.

4. The touchable switch electronic candle with fragrance dispersing function according to claim 3, further comprising a shell body, wherein an outer side of the shell body is provided with a wax layer, and a top end of the wax layer is provided with a groove for accommodating the fragrance dispersing block.

5. The touchable switch electronic candle with fragrance dispersing function according to claim 4, wherein a surface of the fragrance dispersing block is a smooth mirror surface, and fragrance and filler are integrally formed, wherein the filler constitutes the fragrance dispersing block.

6. The touchable switch electronic candle with fragrance dispersing function according to claim 5, wherein the fragrance dispersing block is porous, and the fragrance is filled in pores of the filler constituting the fragrance dispersing block; and
   the touchable switch electronic candle further comprises an essence urging mechanism, wherein the essence urging mechanism facilitates volatilization of the essence in the fragrance dispersing block.

7. The touchable switch electronic candle with fragrance dispersing function according to claim 6, wherein an upper end of the fragrance dispersing block is covered with a decorative layer with micro-pores, and a surface of the decorative layer is a smooth mirror surface.

8. The touchable switch electronic candle with fragrance dispersing function according to claim 6, wherein the essence urging mechanism is a micro-fan, the micro-fan is provided inside the shell body, and an outlet end of the micro-fan is connected to the fragrance dispersing block through an air outlet pipe.

9. The touchable switch electronic candle with fragrance dispersing function according to claim 6, wherein the essence urging mechanism is an electric heating wire, a top end of the shell body is provided with a heat insulation block, the electric heating wire is arranged on a top end of the heat insulation block, and the electric heating wire is in contact with the fragrance dispersing block.

10. The touchable switch electronic candle with fragrance dispersing function according to claim 5, wherein an inside of the shell body is provided with a battery bin, the master control circuit is located inside the shell body, the touch switch circuit is located outside the shell body, a top end of the shell body is provided with a candle head, and the light emitting diode (D1) is located inside the candle head.

11. The touchable switch electronic candle with fragrance dispersing function according to claim 2, further comprising a fragrance dispersing block, wherein an inside of the fragrance dispersing block is filled with essence.

12. The touchable switch electronic candle with fragrance dispersing function according to claim 7, wherein the essence urging mechanism is a micro-fan, the micro-fan is provided inside the shell body, and an outlet end of the micro-fan is connected to the fragrance dispersing block through an air outlet pipe.

13. The touchable switch electronic candle with fragrance dispersing function according to claim 7, wherein the essence urging mechanism is an electric heating wire, a top end of the shell body is provided with a heat insulation block, the electric heating wire is arranged on a top end of the heat insulation block, and the electric heating wire is in contact with the fragrance dispersing block.

14. The touchable switch electronic candle with fragrance dispersing function according to claim 6, wherein an inside of the shell body is provided with a battery bin, the master control circuit is located inside the shell body, the touch switch circuit is located outside the shell body, a top end of the shell body is provided with a candle head, and the light emitting diode (D1) is located inside the candle head.

\* \* \* \* \*